(12) United States Patent
Laurencin et al.

(10) Patent No.: US 8,536,230 B2
(45) Date of Patent: Sep. 17, 2013

(54) METHODS FOR REGULATING GELATION OF POLYSACCHARIDE SOLUTIONS AND USES THEREOF

(75) Inventors: Cato T. Laurencin, Earlysville, VA (US); Lakshmi Sreedharan Nair, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 827 days.

(21) Appl. No.: 12/162,057

(22) PCT Filed: Jan. 25, 2007

(86) PCT No.: PCT/US2007/001896
§ 371 (c)(1),
(2), (4) Date: Jul. 24, 2008

(87) PCT Pub. No.: WO2007/087350
PCT Pub. Date: Aug. 2, 2007

(65) Prior Publication Data
US 2009/0270514 A1    Oct. 29, 2009

Related U.S. Application Data

(60) Provisional application No. 60/762,084, filed on Jan. 25, 2006.

(51) Int. Cl.
*A61K 47/04* (2006.01)
*A61K 47/36* (2006.01)

(52) U.S. Cl.
USPC .......................................... 514/769; 524/777

(58) Field of Classification Search
None
See application file for complete search history.

(56) References Cited

U.S. PATENT DOCUMENTS 6,344,488 B1    2/2002    Chenite et al.

FOREIGN PATENT DOCUMENTS

| CN | 1486753 A | 4/2004 |
|---|---|---|
| CN | 1698902 A | 11/2005 |
| WO | 2007051311 | 5/2007 |

OTHER PUBLICATIONS

Alsarra et al Drug Dev Ind Pharm. May 2005;31(4-5):385-95.*
Ogawa et al Chem. Mater., 1993, 5 (5), pp. 726-728.*
Okuyama et al Carbohydrate Polymers 2000, 41; 237-247.*
Berger, et al., Structure and interactions in covalently and ironically crosslinked chitosan hydrogels for biomedical applications:, EU Journal of Pharmaceutics and Biopharmaceutics, 57 (2004), 19-34.
Hitoshi Sashiwa, et al., "Chemically modified chitin and chitosan as biomaterials", Prog. Polym. Sci. 29 (2004), 887-908.
Giyoong Tae, et al., "Sustained release of human growth hormone from in situ forming hydrogels using self-assembly of fluoroalkyl-ended poly(ethylene glycol)", Biomaterials 26 (2005), 5259-5266.
Hatefi, et al., "Biodegradable injectable in situ forming drug delivery systems", Journal of Controlled Release, 80 (2002), 9-28.
Chenite, et al., "Novel injectable neutral solutions of chitosan form biodegradable gels in situ", Biomaterials 21 (2000), 2155-2161.
Bhattarai, et al., "PEG-grafted chitosan as an injectable thermosensitive hydrogel for sustained protein release", Journal of Controlled Release 103 (2005), 609-624.
Ruel-Gariepy, et al., "A thermosensitive chitosan-based hydrogel for the local delivery of paclitaxel", EU Journal of Pharmaceutics and Biopharmaceutics 57 (2004), 53-63.

* cited by examiner

*Primary Examiner* — Padma V Baskar
(74) *Attorney, Agent, or Firm* — Rodney L. Sparks

(57) ABSTRACT

The present invention provides a method for preparing chitosan solutions to allow regulating the conditions in which the chitosan solution will gel. The present invention also provides methods for using chitosan solutions as compositions and for using chitosan solutions in vitro and in vivo.

24 Claims, 9 Drawing Sheets

METHODS FOR REGULATING GELATION OF POLYSACCHARIDE SOLUTIONS AND USES THEREOF

CROSS REFERENCE TO RELATED APPLICATIONS

This application is a national stage filing of International Application No. PCT/US2007/001896, filed on Jan. 25, 2007, which claims priority from U.S. Provisional Application Ser. No. 60/762,084, filed Jan. 25, 2006, entitled "Methods for Regulating Gelation of Polysaccharide Solutions and Uses Thereof," the disclosures of which are hereby incorporated by reference herein in their entirety.

FIELD OF THE INVENTION

The present invention relates generally to a biocompatible temperature-dependent gelling solution of chitosan and inorganic salts, and methods of preparation and use thereof.

BACKGROUND

Chitin is a naturally abundant mucopolysaccharide which is a (1-4)-β-linked glycan composed of 2-acetamido-2-deoxy D-glucose. Application of chitin is currently limited because of its low solubility in most common organic solvents.

On the other hand, chitosan, which is the N-deacetylated derivative of chitin obtained by the partial or total alkaline deacetylation of chitin, is soluble in acidic aqueous solutions. Chitosan is composed primarily of 2-acetamido-2-deoxy D-glucose and glucosamine residues the aqueous solubility can be attributed to the protonation of the amino groups in acidic environments. It is a pH dependent cationic polysaccharide, which is known to be non-toxic, biocompatible, and biodegradable, with its degradation products being known natural metabolites. Chitosan has been evaluated in a number of medical applications including wound dressings, matrices for controlled drug delivery and as a hemostatic agent.

Chitosan is an N-deacetylated derivative of chitin which is the structural component of crustacean shells and fungal cell walls, and is obtained at a low cost from sea-food processing (Chitin: Fulfilling a Biomaterials Promise: Eugene Khor, Elsevier, Oxford, UK, 2001). The structure of chitin and chitosan are similar to cellulose where, carbon-2 of the cellulose has acetamide or amino groups, for chitin and chitosan respectively. Chitosan is an inert, hydrophilic, biocompatible, and biodegradable polymer and hence are attractive candidates for biomedical and pharmaceutical applications. Chitosan is currently investigated for various applications such as topical ocular application, as a bioadhesive polymer, penetration enhancer by opening epithelial tight-junctions and as wound dressing (Berger, et al., European Journal of Pharmaceutics and Biopharmaceutics 57 (2004) 19-34).

Various chemically modified chitosan derivatives with unique properties have been developed (Hitoshi et al., Prog. Polym. Sci. 29 (2004) 887-908). The excellent biocompatibility of chitosan, combined with its enzymatic biodegradability, makes chitosan an excellent candidate for various in vivo applications. In addition, the low cost of chitosan and its wide availability as a natural waste product, makes chitosan a very attractive polymer for wide range of applications.

Chitosan has been extensively investigated for developing hydrogels with unique properties, due to the hydrophilicity of the base polymer, and the availability of active cross-linkable groups along the polymer chain. These chitosan hydrogels were found to be excellent candidates for a variety of applications, including, controlled release of bioactive/drug molecules, as cell encapsulation matrices, and as tissue engineering scaffolds. Chemical or covalent cross-linking of chitosan making use of mainly the active amino groups along the polymer chain and ionic cross-linking making use of the cationic nature of chitosan aqueous acid solutions, have been extensively investigated for developing hydrogels for various applications.

The different chemical cross-linking agents reported for chitosan include dialdehydes such as glutaraldehyde, diethyl squarate, oxalic acid, and genipin. Apart from these small molecules, functionalized biopolymers such as poly(ethylene glycol diacrylate), oxidized cyclodextrin, telechelic-PVA, PEG dialdehydes and scleroglucan have also been investigated.

In addition to covalent cross-linking, polyelectrolyte complexes of chitosan with a wide range of anionic polymers mainly chitosan alginate system have been extensively investigated for developing drug delivery systems and porous scaffolds for tissue engineering and wound dressings.

Ionic cross-linking of chitosan has been extensively investigated, because it is a simple and mild process with no auxiliary catalyst requirements, and such a procedure has important ramifications for biomedical applications. Metallic anions such as Mo(VI) and Pt(II) have been extensively investigated for ionic cross-linking. Various anions such as sulfates, citrates, oxalates, polyphosphates, and also calcium phosphate, have been tested for the ability to form ionically cross-linked gels with chitosan. All of these ions induce the formation of pure ionic cross-linking, where the chitosan solution instantaneously becomes a gel in the presence of these ions, due to the spontaneity of the ionic reactions.

Recently a novel temperature and pH sensitive gelling system was developed using chitosan in the presence of β-glycerophosphate. In addition to β-glycerophosphate, corresponding sulfates and monosaccharide derivatives were found to exhibit the characteristic properties of β-glycerophosphate (Chenite et al., U.S. Pat. No. 6,344,488; Chenite et al., Biomaterials 21 (2000) 2155-2161; Ruel-Gariepy et al., European Journal of Pharmaceutics and Biopharmaceutics, 57 (2004) 53-63; Ruel-Gariepy et al., J Controlled Release. 82 (2002) 373-383; Molinaro et al., Biomaterials 23 (2002), 2717-2722).

Injectable in situ forming hydrogels are receiving considerable attention for a variety of biomedical applications such as sustained drug delivery, cell encapsulation and as scaffolds for tissue engineering (Tae et al., Biomaterials, 26, 5259-66, 2005). An injectable system offers several advantages including conformal matching of the implant to complex tissue shapes, delivery of large volumes of implant via minimally invasive surgery, improved patient compliance and comfort, and allows for the delivery of sensitive biomolecules and living cells because it is a gentle process. In situ forming hydrogels are potential candidates specifically for developing sustained delivery vehicles for therapeutic proteins with short half lives.

Various materials have been investigated for the development of injectable hydrogel systems based on non-degradable synthetic polymers such as poloxamers, N-isopropylacrylamide and a variety of degradable natural polymers (Hatefi and Amsden, J. Control Rel., 80:9-28, 2002). One of the most extensively investigated natural polymers for hydrogel development is chitosan. Chitosan is an N-acetylated derivative of the natural polymer Chitin. Chitin is the structural component of crustacean shells and fungal cell walls and is the second most abundant natural polymer. Due to the excellent biocompatibility and enzymatic degradability of chitosan, hydrogels based on chitosan have been found to be excellent candidates for a variety of medical and pharmaceutical applications (Berger et al., Eur. J. Pharm. BioPharm., 57:19-34, 2004).

Different types of cross-linking agents have been investigated for developing chitosan hydrogels. These include chemical cross-linking using various aldehydes, ionic cross-linking using various anions, and polyelectrolyte complexes using anionic polymers. Recently much research has gone into developing stimuli sensitive injectable systems based on chitosan. It has been found that addition of certain polyol counterionic monohead salts such as β-glycerophosphate can lead to the development of temperature and pH sensitive gelling systems (Chenite et al, Biomaterials, 21:2155-61, 2000). Grafting poly(ethylene glycol) of appropriate molecular weight to chitosan has been shown to act as a thermogelling system (Bhattarai et al., J. Control Rel. 103:609-624).

There is a long felt need in the art for compositions and methods to prepare and use biocompatible chitosan. The present invention satisfies this need.

SUMMARY OF THE INVENTION

The present invention relates to methods for the preparation of a biocompatible thermo-gelling chitosan and inorganic phosphate/sulphate mixture and the use of such a mixture.

The invention describes the preparation of a temperature setting chitosan solution having neutral pH which could find wide applications in different areas such as an injectable solution for controlled and prolonged delivery of drugs, proteins and growth factors, as tissue adhesive, wound dressing material, injectable fillers, injectable composites, as scaffolds for tissue engineering applications.

The present invention relates to the preparation of a chitosan solution having neutral pH, which can undergo thermogelation at about a physiological temperature and physiological pH. In one aspect, the solution undergoes gelation at near or above physiological temperature. In one aspect, the thermogelling or thermosetting solution can be prepared by mixing chitosan solution in very dilute acetic acid with appropriate amounts of inorganic phosphate salt powder or solution at 0-4° C. with rapid stirring. The addition of salt powder or solution rapidly increases the pH of the acid chitosan solution to near neutral pH. Chitosan solutions are known to precipitate instantaneously as the pH of the solution is raised to above 6.0. However, it has been found that in the presence of the inorganic phosphate described here, the chitosan remains in solution even at neutral pH (~pH 7.0-7.2). When a chitosan solution of the invention is mixed with appropriate inorganic phosphates at low temperature and heated to near physiological temperature (37° C.) or above, the solutions gel. The time required for gelling to occur has been found herein to depend on several factors, including the concentration of the inorganic phosphate salts, concentration of chitosan solution, and the concentration of aqueous acetic acid solution. The final pH of the solution also correlates to regulation of the present thermogelling system. In one aspect, in an efficient gelling chitosan solution, the final pH of the solution should be approximately at least about 6.8.

In one embodiment, the strength of the gels and the water content of the gels can be varied by varying the concentration of the inorganic phosphate salts added, or by diluting the chitosan-inorganic phosphate mixture with distilled/deionized water, phosphate buffer, weak acid-base, or using cell culture medium.

In one embodiment of the invention, thermo-gelling composite systems are useful as, injectable compositions for various applications. The compositions can be developed mixing insoluble solid particulates with a chitosan-inorganic phosphate mixture, or by mixing water-soluble polymer solutions with chitosan-inorganic phosphate mixture.

In one embodiment, the invention provides a non-toxic, biodegradable, biocompatible and rapidly curing system at physiological temperature to use in a clinical or operating room setting.

In one embodiment, the invention provides a temperature induced rapidly curing two component solution which can solidify into a biodegradable gel for various applications.

In one embodiment, the invention provides a temperature induced rapidly curing system which can be used to develop novel blends or composite systems.

In one embodiment, the invention provides a temperature induced rapidly gelling polymer system as an injectable matrix for the controlled and prolonged delivery of drugs, growth factors, therapeutic proteins and peptides.

In one embodiment, the invention provides a temperature induced rapidly gelling polymer system as an injectable plug for therapeutic embolization and chemoembolization.

In one embodiment, the invention provides a method for preparing thermogelling chitosan solutions with variable gelation times. In one aspect, the gelation times are as short as about several minutes. In another aspect, the gelation times are from about 30 minutes to about several hours. In yet another aspect of the invention, gelation times range from about several hours to about 24 to 36 hours.

In one embodiment, the invention provides a temperature induced rapidly gelling polymer system as an injectable scaffold for various tissue engineering applications.

In one embodiment, the invention provides a temperature induced rapidly gelling polymer system as an injectable cell encapsulation system for various applications.

In one embodiment, the invention provides variable gelling time from a few minutes to a few hours depending on the kind of application the material is targeted.

In one embodiment, the invention provides a method to develop hydrogel system having different water content and gel strength depending on the kind of application the material is targeted.

In one embodiment, the invention provides a method to develop cross-linked systems having different architecture such as foams, spheres, fibers.

In one embodiment, the invention provides novel delivery systems. In one aspect, the present invention provides methods and composition for delivering cells, chondrocytes, stem cells, genes, matrix materials, drugs, proteins, and chemicals. Delivery of bioactive molecules such as nucleic acid molecules encoding a protein can be significantly enhanced by immobilization of the bioactive molecule in a composition of the invention adjacent to the cells where delivery is desired.

In one embodiment, the invention provides methods for administering novel delivery systems. In one aspect, the novel delivery systems are administered to treat diseases, disorders, and conditions in subjects in need thereof. In one aspect, the invention is useful for treating a musculoskeletal-associated disease or disorder. Musculoskeletal-associated diseases or disorders are described herein or are known in the art. In one aspect, the method is useful for enhancing bone repair. In another aspect, the method is useful for treating a bone-associated disease or disorder. In one aspect, treatment of a bone-associated disease or disorder can be done in conjunction with a surgical procedure. In one embodiment, the present invention provides methods and compositions for fabricating three-dimensional structures. In one aspect, the present invention provides various fabrication techniques.

One of ordinary skill in the art would appreciate that various fabrication techniques are available to practice the methods of the invention.

In one embodiment, the present invention provides compositions and methods for tissue regeneration. In one aspect, the tissues are selected from the group consisting of bone and spine.

In one embodiment, the compositions and methods of the invention are useful for tissue engineering.

In one embodiment, the compositions and methods of the invention are useful for preparing composites with organic or inorganic components.

In one embodiment, the compositions and methods of the invention are useful in cell and tissue culture systems. In one aspect, the invention provides methods for encapsulating cells.

The skilled practitioner, practicing the invention, could find wide applications for this thermo-gelling solution. Such applications include use as scaffolds for tissue engineering applications, as tissue adhesive, as a wound dressing material, as injectable fillers or composites, and as an injectable solution for controlled and prolonged delivery of drugs, proteins, and growth factors. The invention provides advantages of a workable, flowable, injectable liquid at colder temperatures along with the advantages of a biocompatible viscous gel at higher, physiological temperatures. The teachings of the present invention also overcome limitations of the prior art by providing for simple, mild, and gentle cross-linking agents at lower concentrations than required by the prior art.

In one aspect, the present invention features a solution of chitosan and inorganic salt maintained at a temperature below about 10° C. that forms a gel as the temperature rises to within a temperature range from about 20° C. to about 50° C. In one aspect, the temperature for gelling is from about 30° C. to about 40° C. The thermo-gelling solution has a pH between about 6.0 and about 8.0.

In one embodiment, the thermo-gelling solution comprises a solution of chitosan and inorganic phosphate or sulfate salts. In a preferred embodiment, the thermo-gelling solution comprises a solution of chitosan and ammonium hydrogen phosphate. In one embodiment, the thermo-gelling solution comprises between about 0.05 weight % and about 10.0 weight % chitosan and between about 0.5 weight % and about 2.8 weight % ammonium hydrogen phosphate. In embodiment, the thermo-gelling solution comprises a ratio of chitosan to ammonium hydrogen phosphate between about 1 and about 3.5.

In another embodiment, the thermo-gelling solution is a solution at a pH between about 6.5 and about 7.5. In a more preferred embodiment, the thermo-gelling solution is a solution at a pH between about 6.8 and about 7.3. In a most preferred embodiment, the thermo-gelling solution is a solution at a pH between about 7.0 and about 7.2

In another embodiment, the thermo-gelling solution is a solution maintained at a temperature below about 5° C. In a currently preferred embodiment, the thermo-gelling solution is maintained at a temperature between about 0° C. and about 4° C.

In a further embodiment, the thermo-gelling solution forms a gel as the temperature rises to within a temperature range from about 35° C. to about 45° C. In a more preferred embodiment, the thermo-gelling solution forms a gel within a temperature range from about 35° C. to about 40° C. In a most preferred embodiment, the thermo-gelling solution forms a gel at a temperature of about 37° C.

The invention further encompasses chitosan of varied molecular weights. In one aspect, chitosan from about 20,000 to about 250,000 is encompassed within the methods described herein.

In accordance with the present invention, there is also provided a pharmaceutical composition comprising a thermo-gelling solution of chitosan and inorganic salts and insoluble solid particulates or water-soluble substances. There is also provided a method for administering the pharmaceutical composition comprising injecting or applying the pharmaceutical composition.

In accordance with the present invention, there is also provided a method of preparing a thermo-gelling solution of the present invention, which comprises the steps of (a) dissolving chitosan within an acidic aqueous solution to obtain an aqueous chitosan solution; (b) maintaining the aqueous chitosan solution at a temperature below about 10° C.; and (c) dissolving an inorganic salt in the aqueous chitosan solution to obtain a thermo-gelling solution, wherein the thermo-gelling solution is a solution at pH between about 6.0 and about 8.0 and forms a gel within a temperature range of about 30° C. to about 50° C.

In one embodiment, an inorganic salt includes inorganic phosphate and/or sulfate salts. In a preferred embodiment, an inorganic salt is ammonium hydrogen phosphate.

In another preferred embodiment, the aqueous chitosan solution comprises between about 0.5 weight % and about 3.5 weight % chitosan.

In another preferred embodiment, the thermo-gelling solution is a solution having a concentration between about 0.5 weight % and about 2.8 weight % ammonium hydrogen phosphate. In still another preferred embodiment steps (a), (b), and (c) yield a thermo-gelling solution having a ratio of chitosan to ammonium hydrogen phosphate between about 1 and about 3.5.

In a further embodiment, steps (a), (b), and (c) yield a thermo-gelling solution at pH between about 6.5 and about 7.5. In a more preferred embodiment, steps (a), (b), and (c) yield a thermo-gelling solution at pH between about 6.8 and about 7.3. In a most preferred embodiment, steps (a), (b), and (c) yield a thermo-gelling solution at pH between about 7.0 and about 7.2.

In a further embodiment, the aqueous chitosan solution is maintained below about 5° C. In a currently preferred embodiment, the aqueous chitosan solution is maintained between about 0° C. and about 4° C.

In a still further embodiment, the thermo-gelling solution formed by steps (a), (b), and (c) forms a gel as the temperature rises to within a temperature range from about 35° C. to about 45° C. In a more preferred embodiment, the thermo-gelling solution forms a gel within a temperature range from about 35° C. to about 40° C. In a most preferred embodiment, the thermo-gelling solution forms a gel at a temperature of about 37° C.

In accordance with the present invention there are also provided methods of using the thermo-gelling solution of the present invention. The invention provides a method of delivering the thermo-gelling solution as an injectable scaffold for tissue engineering comprising injecting an effective amount of the thermo-gelling solution.

The invention further provides a method for delivering one or more substances from the group consisting of cells, fibroblasts, chondrocytes, osteogenic cells, stem cells, genes, drugs, proteins, chemicals, bioactive molecules, growth factors, and therapeutic proteins and peptides comprising administering the thermo-gelling solution as an injectable matrix for the delivery of these substances.

The invention still further provides a method for providing the thermo-gelling solution as an injectable plug for therapeutic embolization and chemoembolization comprising injecting the thermo-gelling solution as an injectable plug for therapeutic embolization and chemoembolization.

BRIEF SUMMARY OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 8, comprising FIGS. 8A to 8C, graphically illustrates the results of in vitro release studies. The ordinates represent cumulative release (in percent) and the abscissa represents time in hours.

FIG. 10, comprising

FIG. 12, comprising

FIG. 14, comprising

FIG. 17, comprising

FIG. 18, comprising

DETAILED DESCRIPTION OF THE INVENTION

Definitions

Figure 1:
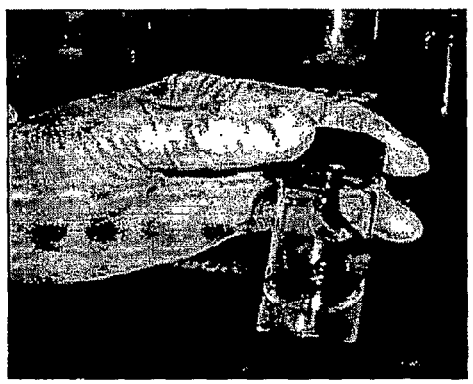
FIG. 1 demonstrates an image of a photomicrograph of a chitosan solution.

In describing and claiming the invention, the following terminology will be used in accordance with the definitions set forth below.

The articles "a" and "an" are used herein to refer to one or to more than one (i.e., to at least one) of the grammatical object of the article. By way of example, "an element" means one element or more than one element.

As used herein, the term "affected cell" refers to a cell of a subject afflicted with a disease or disorder, which affected cell has an altered phenotype relative to a subject not afflicted with a disease or disorder.

Cells or tissue are "affected" by a disease or disorder if the cells or tissue have an altered phenotype relative to the same cells or tissue in a subject not afflicted with a disease or disorder.

A disease, condition, or disorder is "alleviated" if the severity of a symptom of the disease, condition, or disorder, or the frequency with which such a symptom is experienced by a subject, or both, are reduced.

As used herein, an "analog" of a chemical compound is a compound that, by way of example, resembles another in structure but is not necessarily an isomer (e.g., 5-fluorouracil is an analog of thymine).

The term "biocompatible", as used herein, refers to a material that does not elicit a substantial detrimental response in the host.

The terms "cell," "cell line," and "cell culture" as used herein may be used interchangeably. All of these terms also include their progeny, which are any and all subsequent generations. It is understood that all progeny may not be identical due to deliberate or inadvertent mutations.

A "control" cell, tissue, sample, or subject is a cell, tissue, sample, or subject of the same type as a test cell, tissue, sample, or subject. The control may, for example, be examined at precisely or nearly the same time the test cell, tissue, sample, or subject is examined. The control may also, for example, be examined at a time distant from the time at which the test cell, tissue, sample, or subject is examined, and the results of the examination of the control may be recorded so that the recorded results may be compared with results obtained by examination of a test cell, tissue, sample, or subject. The control may also be obtained from another source or similar source other than the test group or a test subject, where the test sample is obtained from a subject suspected of having a disease or disorder for which the test is being performed.

A "test" cell, tissue, sample, or subject is one being examined.

A "pathoindicative" cell, tissue, or sample is one which, when present, is an indication that the animal in which the cell, tissue, or sample is located (or from which the tissue was obtained) is afflicted with a disease or disorder. By way of example, the presence of one or more breast cells in a lung tissue of an animal is an indication that the animal is afflicted with metastatic breast cancer.

A tissue "normally comprises" a cell if one or more of the cell are present in the tissue in an animal not afflicted with a disease or disorder.

A "compound," as used herein, refers to a polypeptide, an isolated nucleic acid, or other agent or drug used in the method of the invention.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health. One of ordinary skill in the art would understand that conditions caused by injury or insult to a tissue are encompassed within disorder.

The use of the word "detect" and its grammatical variants is meant to refer to measurement of the species without quantification, whereas use of the word "determine" or "measure" with their grammatical variants are meant to refer to measurement of the species with quantification. The terms "detect" and "identify" are used interchangeably herein.

As used herein, a "detectable marker" or a "reporter molecule" is an atom or a molecule that permits the specific detection of a compound comprising the marker in the presence of similar compounds without a marker. Detectable markers or reporter molecules include, but are not limited to, radioactive isotopes, antigenic determinants, enzymes, nucleic acids available for hybridization, chromophores, fluorophores, chemiluminescent molecules, electrochemically detectable molecules, and molecules that provide for altered fluorescence polarization or altered light scattering.

As used herein, a "derivative" of a compound refers to a chemical compound that may be produced from another compound of similar structure in one or more steps, as in replacement of H by an alkyl, acyl, or amino group.

As used herein, an "effective amount" means an amount sufficient to produce a selected or desired effect.

The term "encapsulated", as used herein, refers to cells or compounds or materials which are within a thermo-gel which has transitioned to the gel state from the liquid form. Once a gel has formed, it can be cut, molded, or manipulated to form "plugs" or other useful shapes.

The term "enhancing bone repair" as used herein refers to methods of speeding up or inducing better bone repair using compounds of the invention, relative to the speed or amount of bone repair that occurs without administration of compounds of the invention.

The term "inhibit," as used herein, refers to the ability of a compound of the invention to reduce or impede a described function. Preferably, inhibition is by at least 10%, more preferably by at least 25%, even more preferably by at least 50%, and most preferably, the function is inhibited by at least 75%.

As used herein "injecting or applying" includes adminstration of a compound of the invention by any number of routes and means including, but not limited to, topical, oral, bucca, intravenous, intramuscular, intra arterial, intramedullary, intrathecal, intraventricular, transdermal, subcutaneous, intraperitoneal, intranasal, enterial, topical, sublingual, vanginal, ophthalmic, pulmonary, or rectal means.

The term "in situ gelation" refers herein to the thermogelling of chitosan/phosphate gels once the chitosan/phosphate solution is administered within specific sites of a subject. Such sites include, but are not limited to, any tissues, body cavities, muscles, fractures or bone defects, ligaments, cartilages or organs. The thermogelling of the chitosan/phosphate solution is induced by the physiological temperature.

As used herein, an "instructional material" includes a publication, a recording, a diagram, or any other medium of expression which can be used to communicate the usefulness of the peptide of the invention in the kit for effecting alleviation of the various diseases or disorders recited herein. Optionally, or alternately, the instructional material may describe one or more methods of alleviating the diseases or disorders in a cell or a tissue of a mammal. The instructional material of the kit of the invention may, for example, be affixed to a container which contains the identified compound invention or be shipped together with a container which contains the identified compound. Alternatively, the instructional material may be shipped separately from the container with the intention that the instructional material and the compound be used cooperatively by the recipient.

The term "material" as used herein refers to synthetic and natural materials such as matrix components. The term "materials and compounds" as used herein, refers to, inter alia, materials, compounds, cells, peptides, nucleic acids, drugs, matrix components, and imaging agents.

A "mold" is a frame or model that shapes the gel system. Gels can be produced in, but are not limited to, glass or plastic-beakers, dishes, tubes or between two plates so as to obtain any expected shape.

The term "musculoskeletal" as used herein encompasses the general broad meaning of the term, i.e., an organ system that gives a subject the ability to physically move, by using the muscles and skeletal system. Apart from locomotion, the skeleton also lends support and protects internal organs. Musculoskeletal diseases include, but are not limited to, diseases of the muscles and their associated ligaments, and other connective tissue and of the bones and cartilage viewed collectively. Musculoskeletal disorders, include, for example, problems such as low back pain, joint injuries and repetitive strain injuries of various sorts.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

A "sample," as used herein, refers preferably to a biological sample from a subject, including, but not limited to, normal tissue samples, diseased tissue samples, biopsies, blood, saliva, feces, semen, tears, and urine. A sample can also be any other source of material obtained from a subject which contains cells, tissues, or fluid of interest. A sample can also be obtained from cell or tissue culture.

As used herein, "scaffold" refers to a supporting framework, such as one for bone or tissue growth, either in vivo or in vitro.

The term "standard," as used herein, refers to something used for comparison. For example, it can be a known standard agent or compound which is administered or added to a control sample and used for comparing results when measuring said compound in a test sample. Standard can also refer to an "internal standard", such as an agent or compound which is added at known amounts to a sample and is useful in determining such things as purification or recovery rates when a sample is processed or subjected to purification or extraction procedures before a marker of interest is measured.

A "subject" of analysis, diagnosis, or treatment is an animal. Such animals include mammals, preferably a human. Non-human animals subject to diagnosis or treatment include, for example, livestock and pets.

The term "substantially pure" describes a compound, e.g., a protein or polypeptide which has been separated from components which naturally accompany it. Typically, a compound is substantially pure when at least 10%, more preferably at least 20%, more preferably at least 50%, more preferably at least 60%, more preferably at least 75%, more preferably at least 90%, and most preferably at least 99% of the total material (by volume, by wet or dry weight, or by mole percent or mole fraction) in a sample is the compound of interest. Purity can be measured by any appropriate method, e.g., in the case of polypeptides by column chromatography, gel electrophoresis, or BPLC analysis. A compound, e.g., a protein, is also substantially purified when it is essentially free of naturally associated components or when it is separated from the native contaminants which accompany it in its natural state.

A "thermal-sensitive" gel system undergoes a phase transition when induced by temperature.

The term "three-dimensional" refers to the fact that the chitosan solution is simultaneously gelled and shaped by the mold wherein the solution was initially poured.

As used herein, the term "treating" includes prophylaxis of the specific disorder or condition, or alleviation of the symptoms associated with a specific disorder or condition and/or preventing or eliminating said symptoms. A "prophylactic" treatment is a treatment administered to a subject who does not exhibit signs of a disease or exhibits only early signs of the disease for the purpose of decreasing the risk of developing pathology associated with the disease.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered.

As used herein, "thermo-gelling" refers to the formation of a colloidal gel from solution as temperature increases.

As used herein, the term "treating" includes prophylaxis of the specific disease, disorder, or condition, or alleviation of the symptoms associated with a specific disease, disorder, or condition and/or preventing or eliminating said symptoms.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as, cosmids, plasmids (e.g., naked or contained in liposomes) and viruses that incorporate the recombinant polynucleotide.

Chemical Definitions

The compounds of the present invention contain one or more asymmetric centers in the molecule. In accordance with the present invention a structure that does not designate the stereochemistry is to be understood as embracing all the various optical isomers, as well as racemic mixtures thereof.

The general chemical terms used in the description of the compounds of the present invention have their usual meanings. For example, the term "alkyl" by itself or as part of another substituent means a straight or branched aliphatic chain having the stated number of carbon atoms.

As used herein, "inorganic salts" refers to any inorganic ionic compound composed of positively charged cations and negatively charged anions, so that the product is neutral and without a net charge. Such inorganic salts include, but are not limited to, inorganic sulfate or phosphate salts, such as ammonium hydrogen phosphate. Other equivalent substances would also be suitable. Identification of equivalents is well within the skill of the ordinary practitioner and would require no more than routine experimentation. In addition, such inorganic salts may be in solid form or dissolved in solution.

The term, "parenteral" means not through the alimentary canal but by some other route such as subcutaneous, intramuscular, intraspinal, or intravenous.

The compounds of the present invention may exist in tautomeric forms and the invention includes both mixtures and separate individual tautomers. For example the following structure:

is understood to represent a mixture of the structures:

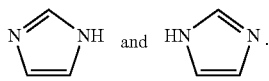

The term "pharmaceutically-acceptable salt" refers to salts which retain the biological effectiveness and properties of the compounds of the present invention and which are not biologically or otherwise undesirable. In many cases, the compounds of the present invention are capable of forming acid and/or base salts by virtue of the presence of amino and/or carboxyl groups or groups similar thereto.

Pharmaceutically-acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, dibeteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like.

Also included are amines where the two or three substituents, together with the amino nitrogen, form a heterocyclic or heteroaryl group Examples of suitable amines include, by way of example only, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like It should also be understood that other carboxylic acid derivatives would be useful in the practice of this invention, for example, carboxylic acid amides, including carboxamides, lower alkyl carboxamides, dialkyl carboxamides, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

The present invention concerns a novel thermo-gelling chitosan solution that remains liquid at lower temperatures but gels at higher temperatures and requires a lower concentration of cross-linking agents relative to the prior art. The present invention relates to a biocompatible thermo-gelling solution of chitosan and inorganic salts and methods for the preparation of and the use of such a solution.

The thermo-gelling solution of the present invention can be prepared by mixing chitosan solution in very dilute acetic acid with appropriate amounts of inorganic salts, such as phosphate or sulfate salt powder or solution, at a low temperature, such as between about 0° C. and about 4° C., with rapid stirring. The addition of salt powder or solution rapidly increases the pH of the acidic chitosan solution to a pH between about 6.0 and about 8.0.

Chitosan solutions are known generally to precipitate instantaneously as the pH of the solution is raised to above about 6.0. However, it has been found that in the presence of the inorganic phosphate described here the chitosan remains in solution even at about neutral pH between about 7.0 and about 7.2, so long as the solution is maintained at a temperature below about 10° C. When chitosan solutions are mixed with appropriate inorganic phosphates at low temperatures and are then heated to near-physiological temperatures, such as about 37° C., the solutions gel. The thermo-gelling solution of the present invention forms a gel within a temperature range from about 30° C. to about 50° C. This temperature range is not intended to be exclusive of other temperatures where the thermo-gelling solution of the present invention may form a gel. On the other hand, the thermo-gelling solution of the present invention may also gel at temperatures above or below the temperature range from about 30° C. to about 50° C. However, the thermo-gelling solution of the present invention certainly gels at a temperature within this range, which encompasses near-physiological temperatures.

The time of gelling has been found to depend on several factors including the concentration of the inorganic phosphate salts, concentration of chitosan solution and concentration of aqueous acetic acid solution. The final pH of the solution also correlates with the gelling time of the present thermo-gelling system. In one aspect, the pH of the final solution should be between about 6.0 and about 8.0. For efficiently gelling chitosan solutions, the final pH of the solution has been found to be equal to or higher than 6.8.

The time of gelling has been found to be independent of storage time and dilution of the solution. The thermo-gelling solution of the present invention has been found to be stable when stored over time at temperatures below about 5° C. Dilution of the thermo-gelling chitosan-inorganic salt solution has also been found not to significantly affect the gelling time of the solution. Because dilution does not significantly affect gelling times, thermo-gelling systems may be developed which will enable the formation of gels of different strengths and water contents for various applications. It has been found that the strength of the gels and the water content of the gels can be varied by varying the concentration of the inorganic phosphate salts added or by diluting the chitosan-inorganic phosphate mixture with distilled water, phosphate buffer, or cell culture media. In one embodiment, the present invention provides a method to develop a thermo-gelling system having different water content and gel strength depending on the planned application.

The present invention is also directed to pharmaceutical compositions comprising the compounds of the present invention. More particularly, such compounds can be formulated as pharmaceutical compositions using standard pharmaceutically acceptable carriers, fillers, solubilizing agents and stabilizers known to those skilled in the art. For example, a pharmaceutical composition comprising a compound of the invention, or analog, derivative, or modification thereof, as described herein, is used to administer the appropriate compound to a subject.

Pharmaceutical compositions comprising a compound of the invention are administered to a subject in need thereof by any number of routes and means including, but not limited to, topical, oral, buccal, intravenous, intramuscular, intra arterial, intramedullary, intrathecal, intraventricular, transdermal, subcutaneous, intraperitoneal, intranasal, enteral, topical, sublingual, vaginal, ophthalmic, pulmonary, or rectal means. The oral route is typically employed for most conditions requiring the compounds of the invention. Preference is given to intravenous injection or infusion for the acute treatments. For maintenance regimens, the oral or parenteral, e.g. intramuscular or subcutaneous, route is preferred.

In accordance with one embodiment, a composition is provided that comprises a compound of the invention, or an analog, derivative, or modification thereof, and albumin, more particularly, the composition comprises a compound of the present invention, a pharmaceutically acceptable carrier and 0.1-1.0% albumin. Albumin functions as a buffer and improves the solubility of the compounds. In one aspect, albumin is not added.

In one embodiment, the pharmaceutical compositions useful for practicing the invention may be administered to deliver a dose of between 1 ng/kg/day and 100 mg/kg/day. In another embodiment, the pharmaceutical compositions useful for practicing the invention may be administered to deliver a dose of between 1 ng/kg/day and 100 g/kg/day.

Pharmaceutically acceptable carriers which are useful include, but are not limited to, glycerol, water, saline, ethanol, and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey).

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non toxic parenterally acceptable diluent or solvent, such as water or 1,3 butane diol, for example. Other acceptable diluents and solvents include, but are not limited to, Ringer's solution, isotonic sodium chloride solution, and fixed oils such as synthetic mono- or di-glycerides.

Compounds which are identified using any of the methods described herein, or are useful with the methods described herein, may be formulated and administered to a subject for treatment of any of the diseases and disorders described herein. However, the use of compounds of the invention should not be construed to include only the diseases and disorder described herein. Preferably, the subject is a human.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts.

Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, and mammals, including commercially relevant mammals such as cattle, pigs, horses, sheep, cats, and dogs.

A pharmaceutical composition of the invention may be prepared, packaged, or sold in bulk, as a single unit dose, or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents. Particularly contemplated additional agents include anti-emetics and scavengers such as cyanide and cyanate scavengers.

Controlled- or sustained-release formulations of a pharmaceutical composition of the invention may be made using conventional technology.

In some cases, the dosage forms to be used can be provided as slow or controlled-release of one or more active ingredients therein using, for example, hydropropylmethyl cellulose, other polymer matrices, gels, permeable membranes, osmotic systems, multilayer coatings, microparticles, liposomes, or microspheres or a combination thereof to provide the desired release profile in varying proportions. Suitable controlled-release formulations known to those of ordinary skill in the art, including those described herein, can be readily selected for use with the pharmaceutical compositions of the invention. Thus, single unit dosage forms suitable for oral administration, such as tablets, capsules, gelcaps, and caplets that are adapted for controlled-release are encompassed by the present invention.

Most controlled-release formulations are designed to initially release an amount of drug that promptly produces the desired therapeutic effect, and gradually and continually release of other amounts of drug to maintain this level of therapeutic effect over an extended period of time. In order to maintain this constant level of drug in the body, the drug must be released from the dosage form at a rate that will replace the amount of drug being metabolized and excreted from the body.

Controlled-release of an active ingredient can be stimulated by various inducers, for example pH, temperature, enzymes, water, or other physiological conditions or compounds.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

As used herein, an "oily" liquid is one which comprises a carbon-containing liquid molecule and which exhibits a less polar character than water.

A formulation of a pharmaceutical composition of the invention suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, a paste, a gel, a toothpaste, a mouthwash, a coating, an oral rinse, or an emulsion. The terms oral rinse and mouthwash are used interchangeably herein.

Injectable formulations may be prepared, packaged, or sold in unit dosage form, such as in ampules or in multi dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen free water) prior to parenteral administration of the reconstituted composition.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. See Genaro, ed., 1985, Remington's Pharmaceutical Sciences, Mack Publishing Co., Easton, Pa., which is incorporated herein by reference.

The compound can be administered to a subject as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type, and age of the subject, etc.

The invention also provides a pharmaceutical pack or kit comprising one or more containers filled with one or more of the ingredients of the pharmaceutical compositions of the invention. In accordance with one embodiment, a kit is provided for treating a subject in need of immuno-modulation. Preferably, the subject is a human. In one embodiment, the kit comprises one or more of the SIP analogs of the present invention and may also include one or more known immunosuppressants. These pharmaceuticals can be packaged in a variety of containers, e.g., vials, tubes, microtiter well plates, bottles, and the like. Other reagents can be included in separate containers and provided with the kit; e.g., positive control samples, negative control samples, buffers, cell culture media, etc. Preferably, the kits will also include instructions for use.

Although any methods and materials similar or equivalent to those described herein can be used in the practice or testing of the present invention, the preferred methods and materials are described herein.

One skilled in the art will readily appreciate that the present invention is well adapted to carry out the objects and obtain the ends and advantages mentioned, as well as those inherent therein. The present invention may be embodied in other specific forms without departing from the spirit or essential attributes thereof and, accordingly, reference should be made to the appended claims, rather than to the foregoing specification, as indicating the scope of the invention.

EXAMPLES

The invention is now described with reference to the following examples. These examples are provided for the purpose of illustration only and the invention should in no way be construed as being limited to these examples, but rather should be construed to encompass any and all variations which become evident as a result of the teachings provided herein.

Development of Thermogelling Chitosan Solution:

It is disclosed herein that the temperature controlled gelling of chitosan solution can be carried out by the addition of inorganic phosphate salts. In the presence of inorganic phosphate salts, it has been found that the method of the invention provides a result which is similar to the result obtained with organic phosphate salts described earlier (Chenite et al., U.S. Pat. No. 6,344,488, Chenite et al., Biomaterials 21 (2000) 2155-2161, Ruel-Gariepy et al., European Journal of Pharmaceutics and Biopharmaceutics, 57 (2004) 53-63, Ruel-Gariepy et al., J Controlled Release. 82 (2002) 373-383, Molinaro et al., Biomaterials 23 (2002), 2717-2722). The present invention also discloses that when using inorganic phosphate salts, the gelling properties of the system can be achieved at lower concentrations of the phosphate salts.

Figure 20:
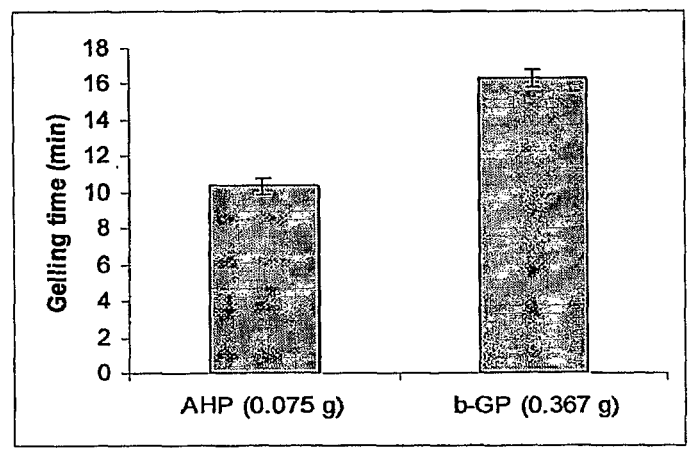
FIG. 20 graphically illustrates the results of studies of the effects of various concentrations of AHP and β-glycerophosphate for inducing thermogelation. As is evident from the graph, the concentration of AHP is significantly lower compared to β-glycerophosphate (β-GP) for inducing thermogelation at 37° C.

A concentrated solution of ammonium hydrogen phosphate (60% solution in distilled water resulting in a pH of approximately 8.3, or finely powdered ammonium hydrogen phosphate (AHP) (by grinding the salt powder using a mortar and pestle) was used for preparing the thermo-gelling solutions (FIG. 20).

Figure 2:
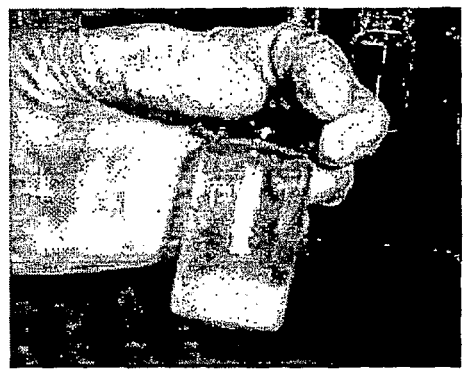
FIG. 2 demonstrates an image of a photomicrograph showing chitosan solution mixed with ammonium hydrogen phosphate (AHP).
Figure 3:
FIG. 3 demonstrates an image of a photomicrograph showing chitosan-AHP solution heated at 37° C. for 4 minutes.
Figure 4:
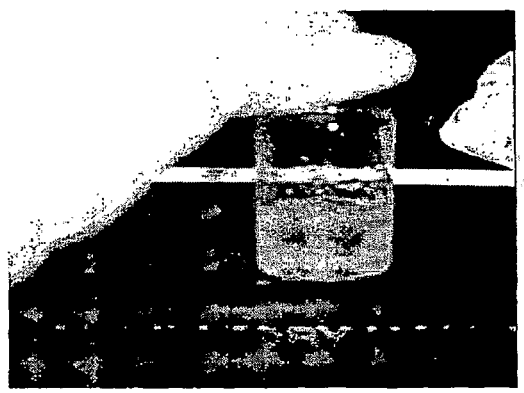
FIG. 4 demonstrates an image of a photomicrograph showing thermo-gelled chitosan-AHP mixture.

The preliminary temperature induced gelling experiments described herein were carried out as follows: A definite volume of chitosan solution in acetic acid was taken in a screw capped glass vial (see FIG. 1). The solution was kept in an ice bath to lower the temperature of the solution. The solution was stirred suing a Teflon magnetic stir bar. To this cold solution was added the required amount of AHP powder (drop by drop in the case of AHP solution) and stirred for 2-5 minutes when a translucent solution was formed (FIG. 2). The solution was then taken out of the ice bath and kept in a water bath heated to 37° C. A stop watch was started at that time. The flowability of the solution was periodically monitored by tilting the vial. After 3-4 minutes (depending on the pH and concentration of AHP added), the solution cleared; however some air bubbles were present (FIG. 3). The viscosity of the solution increased with time and the solution then lost the ability to flow. A transparent to opaque gel (FIG. 4) was formed. The time required for the transparent to opaque gel to form varied from about 9 minutes to 24 hours, depending variables such as the concentration of AHP and the pH of the solution used.

Role of pH:

For developing thermo-gelling solution, the pH of the chitosan solution was found to be very critical as in the case of the glycerol phosphate system (Chenite et al., U.S. Pat. No. 6,344,488; Chenite et al., Biomaterials 21 (2000) 2155-2161; Ruel-Gariepy et al., European Journal of Pharmaceutics and Biopharmaceutics, 57 (2004) 53-63; Ruel-Gariepy et al., J Controlled Release. 82 (2002) 373-383; Molinaro et al., Biomaterials 23 (2002), 2717-2722). Chitosan was obtained from Sigma Aldrich USA and was reported to have a degree of deacetylation of 85%. Chitosan solutions were prepared by dissolving chitosan powder in a 0.5% acetic acid solution (~pH 3.14). In another experiment 1% acetic acid solution was also examined. However, 0.5% acetic acid was found to be appropriate for the present study, as it can raise the pH of the resulting chitosan solution compared to 1% acetic acid. Different concentrations of chitosan solution were examined to determine the feasibility of developing a thermo-gelling system. The different concentrations tested were: 1%, 2%, 2.8%, and 3%. Appropriate concentrations of chitosan were dissolved by magnetic stirring in 0.5% acetic acid solution for 48 hours at room temperature, followed by filtering the solution using a metal sieve to remove un-dissolved material. The pHs of the corresponding solutions are provided in Table 1.

TABLE 1

| Chitosan (wt %) | Acetic acid concentration (%) | ~pH of the solution |
|---|---|---|
| 1% | 0.5% | 4.3 |
| 2% | 0.5% | 5.3 |
| 2% | 1% | 4.26 |
| 2.8-3% | 0.5% | 5.7 |

Chitosan is known to precipitate at pHs above about 6.0. All the chitosan solutions prepared as described above were found to form clear light yellow solutions with no indication of precipitation even after prolonged incubation at room temperature or at physiological temperature.

The addition of AHP solution having an alkaline pH (pH 8.3), or AHP powder, significantly increased the pH of the chitosan solution. Therefore, the pH of the final solution to a certain extent was found to depend on the concentration of inorganic phosphate salt. Table 2 summarizes the approximate pHs of chitosan solutions prepared with different concentrations of AHP. Furthermore, it is disclosed herein that solutions having appreciable gelling properties are formed when the final pH of the gelling solution is adjusted to, or becomes, about 7.0-7.2.

TABLE 2

| Chitosan solution (2.8%) | AHP (solution) in gms | Final pH |
|---|---|---|
| 10 mL | 0.24 | 7.16 |
| 10 mL | 0.18 | 7.11 |
| 10 mL | 0.15 | 7.04 |
| 10 mL | 0.12 | 6.99 |
| 10 mL | 0.06 | 6.68 |

Role of AHP Concentration:

The AHP concentration is described herein as having a significant effect on the time required for gelation to occur, and the temperature at which gelation occurs. Different concentrations of AHP and chitosan were tested by adding AHP as a solution or as a powder, followed by vigorous stirring to develop thermo-gelling solutions. It is disclosed herein that a minimum concentration of AHP is required to develop the thermo-gelling solution. Without wishing to be bound by any particular theory, the present data suggest the importance of phosphate ions in bringing about the cross-linking process. Table 3 summarizes the effect of AHP concentration on the gelling time of various thermo-gelling chitosan solutions.

TABLE 3

| Chitosan solution | Chitosan (mg) | AHP (mg) | pH | Gelling Time |
|---|---|---|---|---|
| 10 mL, 3% | 300 | 180 | 7.11 | ~10 minutes |
| 10 mL, 3% | 300 | 150 | 7.04 | ~12 minutes |
| 10 mL, 3% | 300 | 120 | 6.99 | Did not gel in 30 minutes (Gelled within 24 hours) |
| 10 mL, 3% | 300 | 60 | 6.68 | Did not gel within 24 hours |
| 10 mL, 3% | 300 | 240 | 7.16 | ~10 minutes |
| 5 mL 2.8% | 140 | 75 | 7.11 | ~11 minutes |
| 5 mL 2.8% | 140 | 60 | 7.07 | ~25 minutes |
| 5 mL 2.8% | 140 | 45 | 7.06 | Did not gel within 30 minutes; Gelled within 24 hours) |
| 5 mL 2.8% | 140 | 30 | 6.89 | Did not gel within 24 hours |
| 5 mL 2.8% | 140 | 90 | 7.25 | ~9 minutes |

Role of Temperature on Gelation:

The thermo-gelling chitosan solution described herein is be stable when kept at low temperatures (about 0-4° C.) for a long time. The gelling process will set only when the temperature is raised to room temperature or above. Table 4 summarizes the results of the gelation time at 37° C., for a thermo-gelling solution stored at 4° C. for 24 hours, compared to the gelation time of freshly prepared solutions.

TABLE 4

| Chitosan (mg) | AHP (mg) | Storage time at 4° C. | Gelling time |
|---|---|---|---|
| 140 | 75 | 0 | ~11 minutes |
| 140 | 75 | 24 | ~10 minutes |
| 140 | 60 | 0 | ~25 minutes |
| 140 | 60 | 240 | ~25 minutes |

Effect of Dilution:

In addition to the concentration of AHP and the pH of the solutions, the effect of dilution of the solution using distilled water, 0.01 N sodium hydroxide solution, cell culture medium such as minimum essential medium (MEM), 1% poly(vinyl alcohol), and particulate materials such as hydroxyapatite powder were also studied. Interestingly, the dilution of chitosan-inorganic phosphate solution did not affect significantly the gelling time of the solution. Dilution of the thermogelling solution significantly affected the physical properties such as gel strength. Table 5 shows the gelling time of various diluted solutions of chitosan-inorganic phosphate at 37° C.

TABLE 5

| Chitosan Solution | Chitosan (mg) | AHP (mg) | Solution added | pH | Gelling time |
|---|---|---|---|---|---|
| 5 mL 2.8% | 140 | 75 | 5 ml water (pH 7.0) | 7.11 | ~11 minutes |
| 5 mL 2.8% | 140 | 75 | 2 mL water | 7.1 | ~10 minutes |
| 5 mL 2.8% | 140 | 75 | 9 mL water | 7.1 | ~13 minutes |
| 5 mL 2.8% | 140 | 75 | 2 mL, MEM | 7.1 | ~11 minutes |
| 5 mL 2.8% | 140 | 60 | 2 mL MEM | 7.06 | ~21 minutes |
| 5 mL 2.8% | 140 | 75 | 5 mL, MEM | 7.1 | ~11 minutes |
| 5 mL 2.8% | 140 | 75 | 9 mL MEM | 7.06 | ~11 minutes |
| 5 mL 2.8% | 140 | 75 | 2 mL, 0.01N NaOH | 7.22 | ~11 minutes |
| 5 mL 2.8% | 140 | 50 | 2 mL, 0.01N NaOH | 7.14 | ~4.5 hours |
| 5 mL 2.8% | 140 | 0 | 2 mL, 0.01N NaOH | 6.45 | Did not gel |
| 5 mL 2.8% | 140 | 60 | 2 mL, 0.01N NaOH | 7.13 | ~24 minutes |
| 5 mL 2.8% | 140 | 90 | 1% PVA solution | — | ~9 minutes |
| 5 mL 2.8% | 140 | 90 | 1 g of HAp powder | — | ~9 minutes |

The dilution of chitosan solution using any of the above-mentioned diluting solutions before adding AHP did not show a significant change in the gelling time of the solution as shown in Table 6. This is presumably due to the absence of significant interactions between phosphate ions and chitosan solution at 0-4° C.

TABLE 6

| Chitosan (mg) | Diluting solution | AHP | Diluting solution | pH | Gelling time |
|---|---|---|---|---|---|
| 140 | — | 75 | 5 mL water | 7.11 | ~11 minutes |
| 140 | 5 mL water | 75 | — | 7.08 | ~13 minutes |
| 140 | — | 75 | 2 mL MEM | 7.1 | ~11 minutes |
| 140 | 2 mL MEM | 75 | | 7.06 | ~14 minutes |

Figure 5:
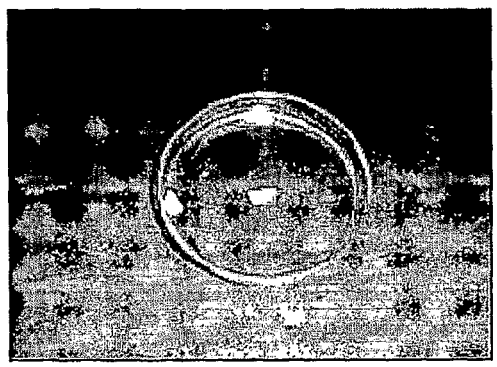
FIG. 5 demonstrates an image of a photomicrograph showing the composite matrix formed from thermogelling chitosan solution and hydroxyapatite.

FIG. 5 illustrates the ability to make composites of thermo-gelling chitosan solution with HAp. The HAp-chitosan gelling solution formed was found to have high formability and injectability and sets to form cylindrical matrices of appreciable strength for various applications.

The osmolarity of the solution is an important parameter that can affect the biological efficacy of injectable solutions. In the thermo-gelling chitosan solution described here, osmolarity of the solution increases with increase in inorganic phosphate content. The ideal osmolarity of biological fluids has been found to be 270 mOsmol/kg-340 mOsmol/kg. Table 7 summarizes the osmolarity with respect to AHP in the thermo-gelling solution.

TABLE 7

| Chitosan Solution | AHP | Osmolarity |
|---|---|---|
| 5 mL 2.8% solution | 75 mg | 340 mOsmol/Kg |
| 5 mL 2.8% solution | 60 mg | 272.4 mOsmol/Kg |
| 5 mL, 2.8% solution + 2 mL water | 75 mg | 243.39 mOsmol/Kg |
| 5 mL, 2.8% solution + 2 mL water | 90 mg | 292.07 mOsmol/Kg |

Encapsulation of Cells

Figure 6:
FIG. 6 demonstrates an image of a photomicrograph showing the injected cell encapsulated thermogelled matrix in culture.

Preliminary encapsulation of cells within the thermo-gelling solution was performed using MC3T3-E1 cells. The cell-thermogelling chitosan suspension was found to be injectable. FIG. 6 demonstrates cell encapsulated gels formed by injecting the suspension into medium maintained at 37° C. The osteoblast cells which are adherent cells, encapsulated within the gel was found to be rounded, however the cells were found to be alive as evidenced from trypan blue inclusion test after 24 hour incubation.

Preparation of thermo-gelling solution:

Chitosan solution (~2.8%, ~pH 5.6) was prepared in diluted acetic acid. The FITC-Dextran was then dissolved in the chitosan solution (1% w/v and 0.5% w/v) with vigorous stirring. The thermo-gelling solution was prepared by dissolving $5.7 \times 10^{-3}$ M of AHP to 3 mL of chitosan solution containing appropriate amounts of dextran with vigorous stirring in an ice bath. The diluted gelling mixture was prepared by adding 0.5 mL of distilled water (pH-7.0) to the AHP-chitosan mixture and stirred vigorously in an ice bath. The respective dextran loaded solutions (0.3 mL each) were poured into plexiglass molds and allowed to set at 37° C. for 24 h.

Figure 7:
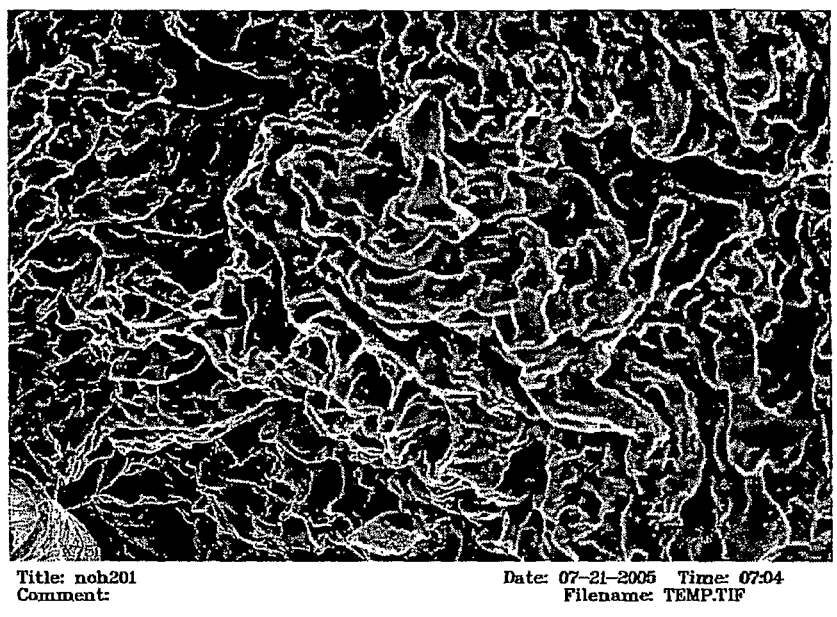
FIG. 7 depicts an image of a scanning electron micrograph of frozen and lyophilized thermo-gel.

The gels were frozen in liquid nitrogen, lyophilized for 24 hours, and then sputter-coated with gold and examined by scanning electron microscopy (SEM) [JSM 6400, JEOL, Boston]. The results are present in FIG. 7.

Figure 8A:
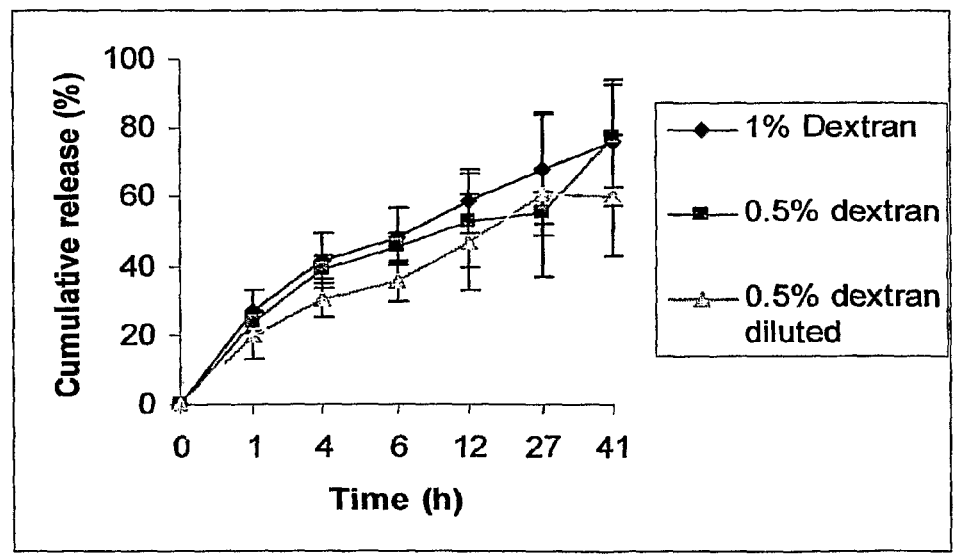
FIG. 8A represents the results of three groups: 1% Dextran, 0.5% Dextran, and 0.5% Dextran diluted.

Injectable, Thermosetting In Situ Forming Biodegradable Hydrogels as Sustained Macromolecular Delivery Systems: In Vitro Release Studies FITC dextran loaded samples (0.5×1 cm) were placed in histology cups and incubated in 50 mL PBS at 37° C. in a shaking water bath. At predetermined time points, 5 mL of the release media was removed and replenished with 5 mL of PBS. The FITC dextran concentration was determined spectrophotometrically and the percentage cumulative release was calculated. The three groups include 1% dextran, 0.5% dextran, and 0.5% dextran diluted. (see FIG. 8A).

Next, varied molecular weights of chitosan (chitosan-FITC) were tested. Chitosan (85% deacetylated), ammonium hydrogen phosphate (AHP) and FITC-dextrans (Mwt, 20,000, 40,000, 150,000 and 250,000) were procured from Sigma-Aldrich, St. Louis, USA. To prepare the thermogelling solution, appropriate concentrations of AHP solution (0.15M-0.068M) were added to chitosan solution (3 mL, 2.8% in dilute acetic acid) in an ice bath with vigorous stirring. The gelling time was determined by incubating the solution in a water bath at 37° C. The flowability of the solution was periodically monitored by tilting the vial. The time at which the solution stopped flowing was noted as the gelling time.

For FITC-dextran loading, appropriate amounts (0.5, 1, and 5% w/v) of FITC-dextrans were dissolved in chitosan-AHP solutions. The respective dextran loaded solutions were poured into petri dishes and allowed to set at 37° C. for 12 h. Circular discs (8 mm diameter) were bored from the thermogelled films for in vitro release studies. Pre-weighed FITC-dextran loaded circular discs were placed in 10 mL of phosphate buffer saline (PBS) at 37° C. in a shaking water bath. At predetermined times the media was removed and replaced with fresh PBS. The FITC-dextran concentration in the release media were determined spectrophotometrically at 491 nm and the percentage cumulative release was calculated based on the total FITC-D content. Statistical significance ($p<0.05$) was determined using one way ANOVA.

Figure 8B:
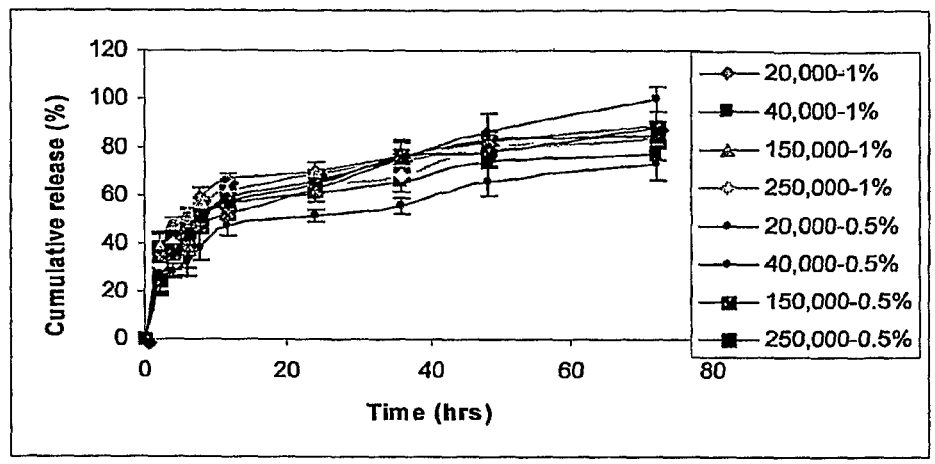
FIG. 8B represent the results of eight groups testing FITC-Dextrans having different molecular weights and at varied concentrations: 20,000-1.0%; 40,000-1.0%; 150,000-1.0%; 250,000-1.0%; 20,000-0.5%; 40,000-0.5%; 150,000-0.5%; 250,000-0.5%.
Figure 8C:
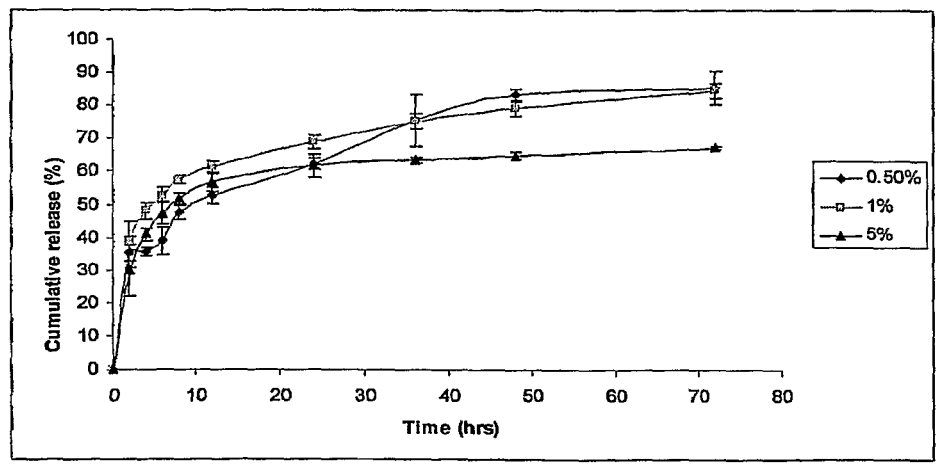
FIG. 8C represents the effects of varied concentrations of FITC-D 150,000 loading on the release profile. The percentages tested were: 0.5%, 1.0%, and 5.0%.

FIGS. 8B and 8C show the effect of dextran molecular weight and percentage loading on the percentage cumulative release. As can be seen from FIG. 8B, the release profiles of FITC-dextrans of different molecular weight do not differ significantly. Even though FITC-D 40,000 showed a decreased release profile compared to FITC-D 20,000 at 0.5% loading, increasing the molecular weight to 150,000 or 250,000 did not show any significant difference in the release profiles of 0.5% and 1% loaded gels. This can be attributed to the micro porous structure of the gels (SEM not shown). Even though lower concentrations of 0.5 and 1% did not show any statistically significant differences, increasing the concentration to 5% resulted in a significant decrease in the release rate as shown in the case of FITC-D 150,000 (FIG. 8C). This is presumably due to the increase in the polymer content of the gel at high concentration resulting in the formation of a more compact gel.

Next, a series of additional experiments was performed. FITC dextran loaded (10, 20, and 30 mg/ml) thermogelling solution were prepared by adding appropriate amounts of FITC-dextran into chitosan-AHP solution (1 ml). The gels were allowed to form by incubating the solutions in a glass vial at 37° C. The formed gels were incubated in 50 mL PBS at 37° C. in a shaking water bath. At predetermined time points, 5 ml of the release media was removed and replenished with 5 mL of PBS. The FITC dextran concentration was determined spectrophotometrically and the percentage cumulative release was calculated (not shown). Curves similar to those in 8A were demonstrated.

Also tested was the release profile of FITC-labeled bovine serum albumin from chitosan-AHP gels represented as the percentage cumulative release. FITC albumin loaded (1, 2, and 3%) thermogelling solution were prepared by adding appropriate amounts of FITC-albumin into chitosan-AHP solution (1 ml). The gels were allowed to form by incubating the solutions in a glass vial at 37° C. The formed gels were incubated in 50 mL PBS at 37° C. in a shaking water bath. At predetermined time points, 5 mL of the release media was removed and replenished with 5 mL of PBS. The FITC albumin concentration was determined spectrophotometrically and the percentage cumulative release was calculated. The data (not shown) demonstrated that the release profiles of FITC-albumin is significantly lower compared to FITC-Dextran of almost similar molecular weight. This is presumably due to the strong interaction of albumin with chitosan matrix compared to a neutral macromolecule such as dextran. This is highly significant as it shows the possibility of the gels to serve as a sustained protein delivery vehicle for various medical and related applications.

SUMMARY

These results demonstrate the potential of injectable, in situ forming chitosan-inorganic salt solutions as a sustained delivery vehicle for macromolecules. A novel injectable thermo-gelling polysaccharide system that can set into a hydrogel at physiological temperature has been developed. The thermo-gelling solutions are found to be stable at low temperature (0-4° C.) and can be rapidly gelled by heating the solution above room temperature preferably 37° C. The setting time can be varied from ~10 minute to 24 hours depending on the composition of the system for appropriate applications. The gel strength of the hydrogels formed can be varied over a wide range by suitable dilutions of the gelling solution as well as by varying the concentration of the reactant molecules. These thermo-gelling solutions can find wide applications including controlled protein, drug, or factor delivery systems, as injectable plugs for therapeutic embolization and chemoembolization, as an injectable scaffold for tissue engineering, as well as a mild cell encapsulation system. Based on the results so far acquired, it can be seen that the concentration of the phosphate to chitosan plays a significant role in forming the gels along with the pH of the resulting solution. Chitosan is a polycationic polymer with high chelating properties. In addition to the charged ammonium groups, the hydroxyl groups along the chains also can react with ionic cross-linkers. Thus, it has already been established that reactions with negatively charged components, either ions or molecules can lead to the formation of ionically bridged cross-linked network. In addition to these ionic interactions, additional physical interactions also play a significant role in forming chitosan gels. These include hydrophobic interactions between chitosan chains and inter-chain hydrogen bonds due to the reduced electrostatic repulsion due to the neutralization of chitosan by the cross-linking ions (Mi et al., J. Polym. Sci. Part B Polym. Phys. 37, 1999, 1551-1564). However, it has been found that if the pH of the chitosan solution is very high, the positive charges of chitosan will be completely neutralized and the system will not form ionic cross-linking on the other hand undergo a coacervation phase separation.

Because it has been found that in the absence of phosphate ion and by changing the pH alone will not allow the thermo-gelling process to take place, the ionic cross-linking via phosphate ions is playing a part in the gelling process. However, since the gelling is taking place only at high pH (~7.0), the possibility of phase inversion and subsequent chitosan chain interactions are also possible. Thus, it can be concluded that different interactions plays a role in bring about the thermosensitivity of the system. It involves ionic cross-linking accompanied with phase inversion process, hydrophobic interaction between chitosan chain and inter-chain hydrogen bonding of chitosan molecules.

Figure 9:
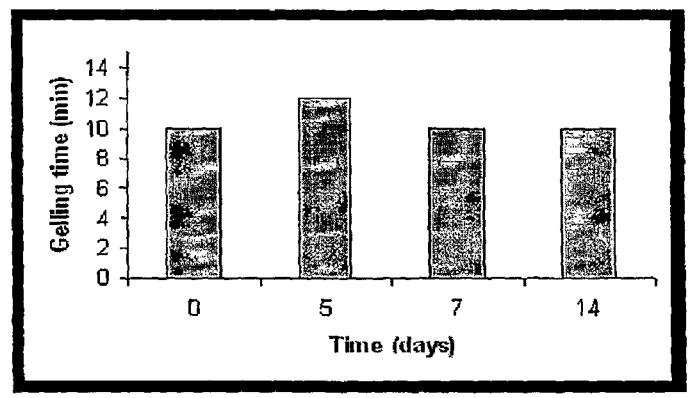
FIG. 9 graphically illustrates the results of studies of the stability of the gelling solution at 4° C. The ordinate indicates gelling time in minutes. The abscissa indicates time of sampling in days.

Stability of the Gelling Solution at 4° C.:

Chitosan solution containing AHP was prepared in an ice bath and stored at 4° C. for various periods of time. Briefly 5 mL of ~2.8% chitosan (Sigma) solution was taken in a glass vial. The solution was then cooled in an ice bath with vigorous stirring. To the cold solution added AHP solution (75 mg) was added. The solution was allowed to stir for another 2 min and stored at 4° C. At predetermined time (5, 7 and 14 days), the solution was taken out and the gelling time was determined by immersing the vials in a water bath kept at 37° C. FIG. 9 shows the gelling time of the solutions after storage for different time periods at 4° C.

Figure 10A:
FIGS. 10A and 10B, represents photographic images of the injectability of the gels.
Figure 10B:
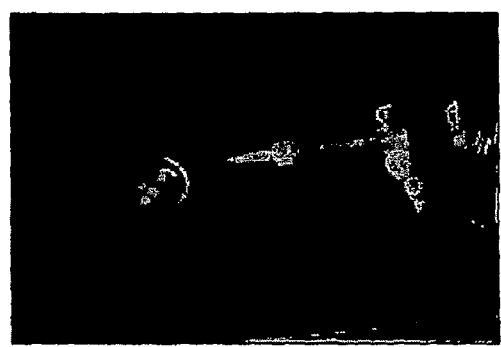
Figure 11:
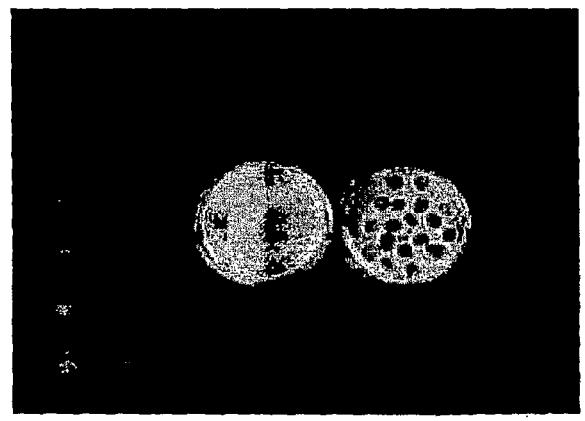
FIG. 11 represents a photographic image showing the ability of the gels to retain encapsulated macromolecules as demonstrated by the encapsulation of FITC-Dextran and the ability to bore circular discs from the FITC-Dextran encapsulated gel, which had been gelled for 24 hours.

Injectability of the Gels:

FIG. 10 shows the injectability of the gels. FIG. 11 shows the ability of the gels to retain encapsulated macromolecules as demonstrated by the encapsulation of FITC dextran and the ability to bore circular discs from the FITC encapsulated gel, gelled for 24 hours at 37° C.

Cell Encapsulation Studies and the viability of the cells within the gels:

Cell encapsulation studies have been performed with, or will be performed with, different cell types: including, but not limited to, human foreskin fibroblasts, bovine smooth muscle cells, rabbit chondrocytes, and MC3T3-E1 osteoblast cells (see also FIG. 6).

The procedure for encapsulation of human foreskin fibroblasts is as shown below:

5 mL of chitosan (2.8% in 0.5% acetic acid: Sigma) was sterilized by autoclaving. The AHP solution (60% in distilled water) was sterilized by filter sterilization using 0.22 μm filter.

The human foreskin fibroblast cells (HFFC) were procured from ATCC and cultured in EMEM supplemented with 10% FBS and 1% antibiotics. Passage 3 cells were trypsinized and counted using a hemocytometer.

The sterilized chitosan (5 mL) was stirred in an ice-bath and to which was added 125 μL of sterile AHP solution. The solution was then stirred well for 2 min in an ice-bath and heated in a water bath at 37° C. for 3-4 min.

Briefly 15 million cells were dispersed in 200 μL of EMEM and to which 2 mL of Chitosan-AHP mixture was added (7.5 million cells/mL). The suspension was triturated well, poured into a sterile petri dish, and allowed to set for 12 hours in an incubator at 37° C., 5% CO2.

After 12 hours of incubation, the formed gel with encapsulated cells was cut into sections using a surgical blasé. The sections were then placed into a 24 well plate and cultured in 1-1.5 mL of EMEM at 37° C.

Figure 12A:
FIGS. 12A and 12B, represents photographic images (20× magnification) of fibroblasts after 1 day in culture during cell encapsulation/viability studies. Live cells are green and dead cells are red.
Figure 12B:
Figure 13:
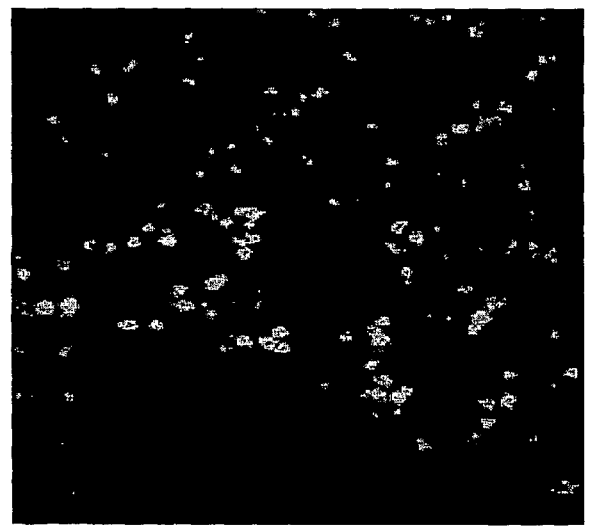
FIG. 13 represents a photographic image (20× magnification) of fibroblasts after 2 days in culture during cell encapsulation/viability studies. Live cells are green and dead cells are red.
Figure 14A:
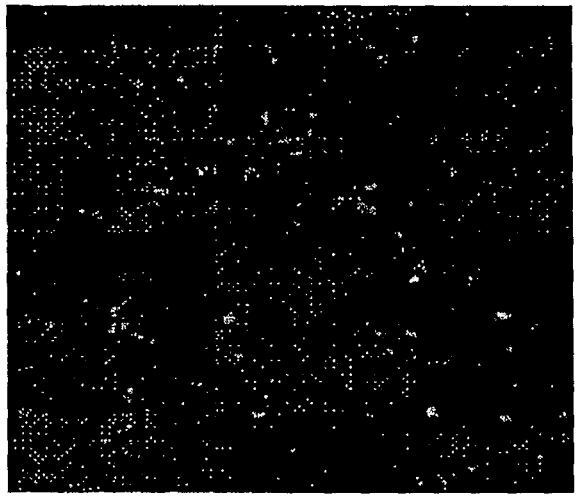
FIGS. 14A and 14B, represents photographic images (20× magnification) of rat preosteoblasts (MC3T3-E1 cells) after 1 day in culture during cell encapsulation/viability studies. Live cells are green and dead cells are red.
Figure 14B:
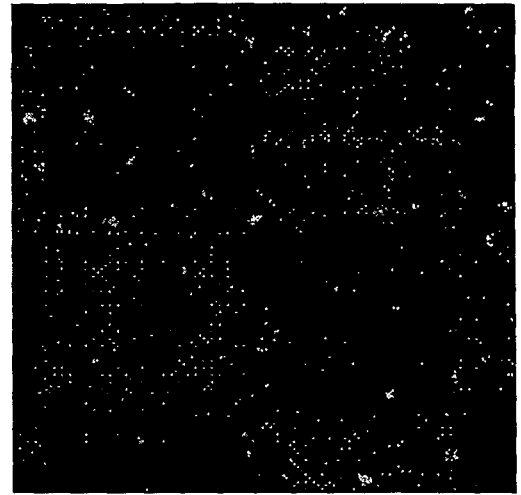

The viability of the encapsulated cells was determined using live dead viability/Cytotoxicity Kit (Molecular Probes, Invitrogen) following the manufacturers instructions. Viability was also determined histologically. Briefly, at predetermined time points the cell encapsulated gels were washed with PBS and incubated in calcein ethidium homodimer mixture (2 μL calcein solution and 2 μL ethidium homodimer-1 and incubated for 40 min at 37° C. Calcein-AM is a non-fluorescent cell permeant fluorescein derivate which is converted by cellular esterase activity into cell impermeant and highly fluorescent calcein. Calcein accumulates inside live cells having intact membranes and results in a green fluorescent signal. Ethidium homodimer-1 enters dead cells with damaged membranes and undergoes a 40 fold enhancement of fluorescence upon binding to their DNA leading to a red fluorescent signal. After 30 min of incubation hydrogel containing cell were observed using BioRad microRadiance Confocal Scanning System (Model #MRA1). FIG. 12 shows the photomicrograph (20×) of fibroblast cells after 1 day in culture. Live cells within the gel are stained green and dead cells stained red. FIG. 13 shows the photomicrograph (20X) of fibroblast cells after 2 days in culture. Live cells within the gel are stained green and dead cells stained red. FIG. 14 shows the photomicrograph (20X) of fibroblast cells after 3 days in culture. Live cells within the gel are stained green and dead cells stained red. Cells were seen to be homogeneously distributed within the gels and almost all cells remained viable after 14 days in culture. See also, FIG. 6.

Figure 15:
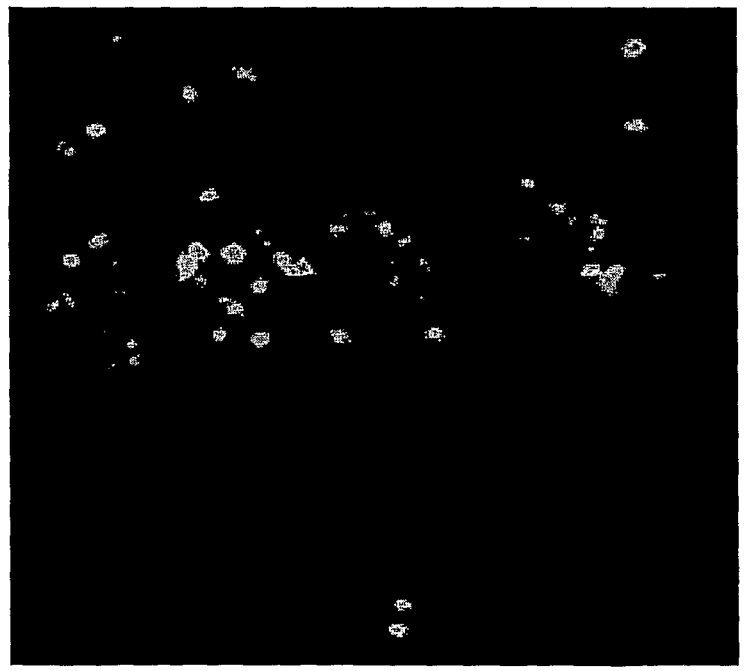
FIG. 15 represents a photographic image (20× magnification) of rat preosteoblasts (MC3T3-E1 cells) after 1 day in culture during cell encapsulation/viability studies at a higher concentration of AHP. Live cells are green and dead cells are red.

Higher Concentrations of AHP:

Attempts were also made to increase the concentration of AHP to study the effect of concentration of AHP on cellular viability. Briefly, sterilized chitosan (3 L) was stirred in an ice-bath and to which was added 125 μL of sterile AHP solution. The solution was then stirred well for 2 min in an ice-bath and heated in a water bath at 37° C. for 3-4 min. Then, $4.3 \times 10^6$ cells were dispersed in 60 μL of EMEM and to which 1 mL of Chitosan-AHP mixture was added. The suspension was triturated well, poured into a sterile petri dish, and allowed to set for 12 h in an incubator at 37° C., 5% $CO_2$. After 12 hours of incubation, the formed gel with encapsulated cells was cut into sections using a surgical blasé. The sections were then placed into a 24 well plate and cultured in 1-1.5 mL of EMEM at 37° C. The viability of the encapsulated cells was determined using live dead viability/Cytotoxicity Kit. FIG. 15 shows the photomicrograph (20X) of fibroblast cells after 1 day in culture and clearly shows the non-toxicity of the higher concentration of AHP used.

Figure 16:
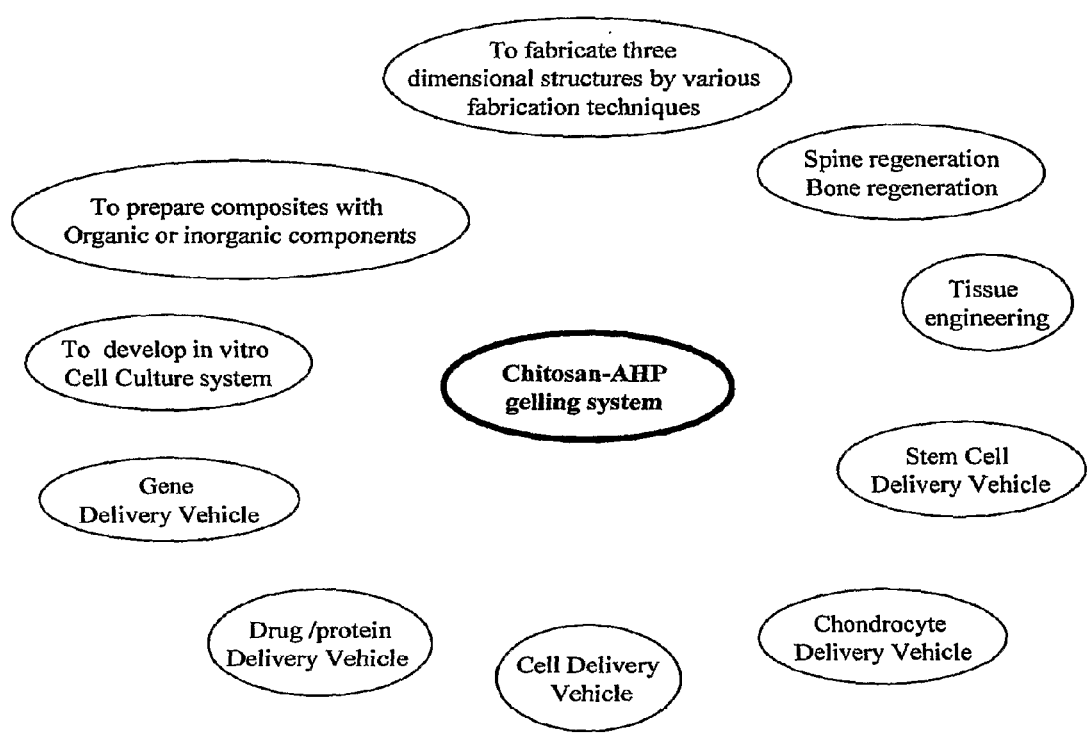
FIG. 16 is a schematic representation of some embodiments of the invention.
Figure 17A:
FIGS. 17A to 17D, represents images of photomicrographs demonstrating the results of experiments on osteogenic differentiation of human mesenchymal stem cells in injectable in situ thermogelling chitosan solution. The images are representative of Live/Dead staining at 7 days (17A and 17C) and at 14 days (17B and 17D) of human mesenchymal stem cells induced to undergo osteogenic differentiation (lower two panels—17C and 17D) or in the presence of control medium (upper two panels—17A and 17D).
Figure 17B:
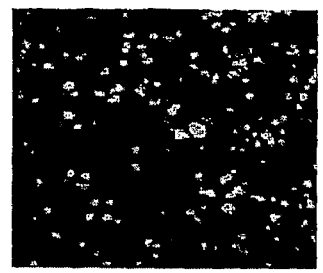
Figure 17C:
Figure 17D:
Figure 18A:
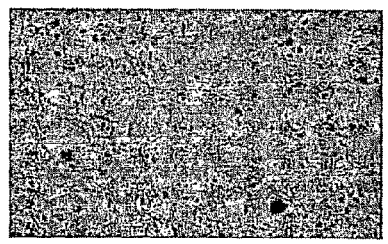
FIGS. 18A to 18D, represents images of photomicrographs demonstrating the results of experiments on osteogenic differentiation of human mesenchymal stem cells in injectable in situ thermogelling chitosan solution. The images represent alizarin red staining of the histological sections of the human mesenchymal stem cell encapsulation at 7 days (18A and 18C) and at 14 days (18B and 18D). 18A and 18D were grown in basal media only. The cells in 18C and 18D were grown in osteogenic differentiation media and differentiation into osteoblasts is evident in the micrographs.
Figure 18B:
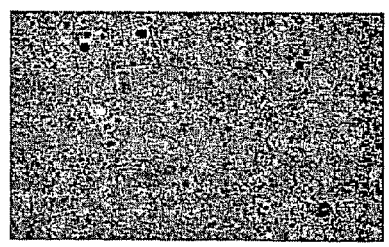
Figure 18C:
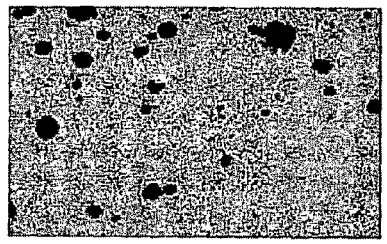
Figure 18D:
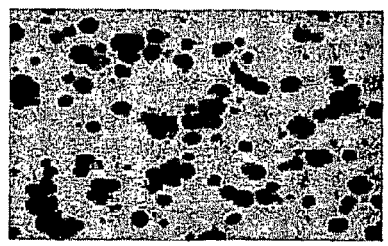

Various embodiments of the invention are schematically illustrated in FIG. 16.

Osteogenic and Adipogenic Differentiation of Human Mesenchymal Stem Cells (hMSCs) in Injectable In Situ Thermogelling Chitosan Solution:

Chitosan and the thermogelling solution were obtained and prepared as above. hMSCs, basal mesenchymal stem cell media, adipogenic differentiation media, and osteogenic differentiation media were obtained from Cambrex (East Rutherford, N.J.).

Encapsulation: The above mixture was equilibrated at 37° C. and the hMSCs were added ($9.2 \times 10^6$ cells/ml of the gelling solution). The cells were uniformly suspended in the chitosan-AHP mixture, and poured into sterile 35 mm diameter plates. The solution was allowed to get at 37° C. in a humidified incubator with 5% $CO_2$. Circular disks were bored from the gel, placed into 24 well plates, and cultured in either basal mesenchymal stem cell media or osteogenic differentiation media. Control gels without cells were prepared in a similar manner.

Live/Dead Viability Assay: The viability of cells encapsulated within the gels after 7 and 14 days was followed by Live/Dead assay (Invitrogen, Carlsbad, Calif.). Briefly, at predetermined time points the medium was removed and circular disks were washed with D-PBS. The disks were then stained with Calcein AM and Ethidium homodimer-1 per the manufacturer's protocol.

Histology: Medium was removed and circular disks were washed with D-PBS and fixed with 1% glutaraldehyde. The gels were paraffin embedded, sectioned, and then stained with Alizarin Red for the presence of calcium according to Armed Forces Institute of Pathology protocols. The gels cultured in adipogenic medium were stained with Oil Red according to a standard procedure.

Results: FIG. 17 demonstrates Live/Dead staining at 7 days (A and C) and at 14 days (B and D). It can be seen that almost all of the hMSCs are alive at 14 days in both the basal hMSC medium (17A and 17B) and the osteogenic differentiation medium (17C and 17D). This indicates that hMSCs survive the cell encapsulation procedure.

FIG. 18 demonstrates alizarin red staining of the histological sections of the HMSC encapsulation at 7 days (A and C) and at 14 days (B and D). Cells grown in the basal medium (18A and 18B) showed minimal differentiation, while cells grown in the osteogenic differentiation medium (18C and 18D) demonstrated a time dependent increase in osteoblasts that were mineralizing.

Figure 19:
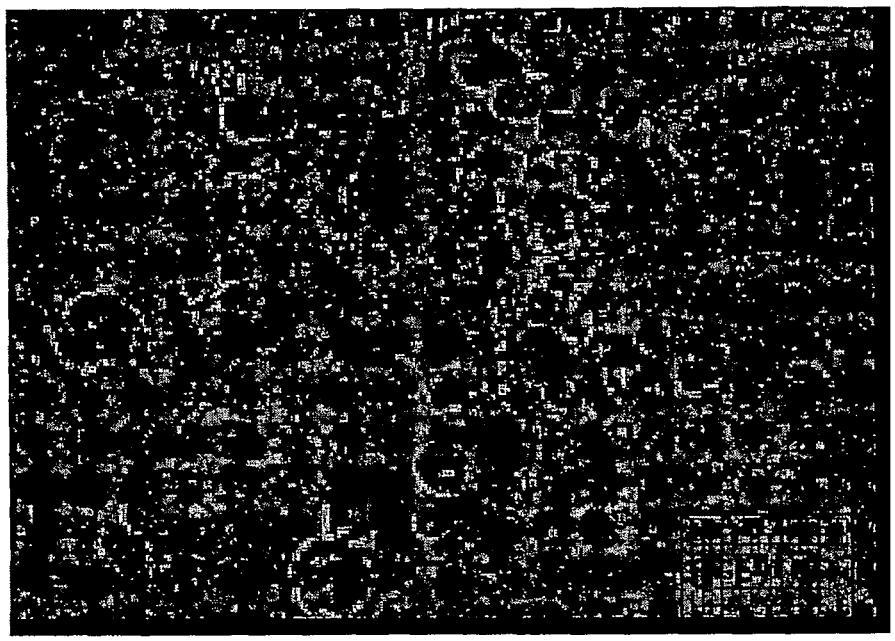
FIG. 19 represents images of photomicrographs demonstrating the results of experiments of adipogenic differentiation of human mesenchymal stem cells in injectable in situ thermogelling chitosan solution. The images represent Oil red staining of the histological sections of human mesenchymal stem cell encapsulation at 28 days cultured in adipogenic medium. The cells grown in adipogenic medium differentiated into adipocytes as evidenced from the histological section.

FIG. 19 demonstrates Oil Red staining of the histological sections of the hMSC encapsulation at 28 days. Cells grown in the adipogenic differentiation medium demonstrated differentiation into adipocytes.

The results demonstrate the potential for injectable chitosan matrices to be used to deliver hMSCs to an osseous defect and that it further supports differentiation into osteoblasts. Such differentiation will allow a bony defect to be filled. This system could be further applied to any surgery currently requiring autograft, subsequently eliminating the morbidity associated with autograft harvest.

The disclosures of each and every patent, patent application, and publication cited herein are hereby incorporated by reference herein in their entirety.

Headings are included herein for reference and to aid in locating certain sections. These headings are not intended to limit the scope of the concepts described therein under, and these concepts may have applicability in other sections throughout the entire specification.

While this invention has been disclosed with reference to specific embodiments, it is apparent that other embodiments and variations of this invention may be devised by others skilled in the art without departing from the true spirit and scope of the invention.

What is claimed is:

1. A thermo-gelling solution-consisting of chitosan and an inorganic salt, wherein the inorganic salt is sulfate or phosphate, wherein said thermo-gelling solution is a solution at a pH between about 6.0 and about 8.0 and at a temperature below about 20° C., further wherein said solution forms a gel within a temperature range from about 20° C. to about 50° C.

2. The thermo-gelling solution of claim 1, wherein said inorganic salt is ammonium hydrogen-phosphate.

3. The thermo-gelling solution of claim 1, wherein said thermo-gelling solution is a solution at a pH between about 6.5 and about 7.5.

4. The thermo-gelling solution of claim 3, wherein said thermo-gelling solution is a solution at a pH between about 7.0 and about 7.2.

5. The thermo-gelling solution of claim 1, wherein said thermo-gelling solution is a solution at a temperature below about 4° C.

6. The thermo-gelling solution of claim 1, wherein said thermo-gelling solution forms a gel within a temperature range from about 25° C. to about 45° C.

7. The thermo-gelling solution of claim 6, wherein said thermo-gelling solution forms a gel within a temperature range from about 30° C. to about 40° C.

8. The thermo-gelling solution of claim 7, wherein said thermo-gelling solution forms a gel at a temperature of about 37° C.

9. The thermo-gelling solution of claim 2, wherein the concentration of chitosan ranges from about 0.05% to about 10.0% and the concentration of ammonium hydrogen phosphate ranges from about 0.16 M to about 0.06 M.

10. The thermo-gelling solution of claim 9, wherein the concentration of chitosan ranges from about 1.0% to about 5.0% chitosan.

11. The thermo-gelling solution of claim 9 comprising a ratio of chitosan to ammonium hydrogen phosphate between about 1.0 and about 3.5.

12. A thermo-gelling solution consisting of chitosan, an inorganic salt, wherein the inorganic salt is sulfate or phosphate and a compound, wherein said thermo-gelling solution is a solution at a pH between about 6.0 and about 8.0 and at a temperature below about 20° C., further wherein said solution forms a gel within a temperature range from about 20° C. to about 50° C., wherein said solution is an aqueous acidic solution.

13. The thermo-gelling solution of claim 1 or 12, wherein said chitosan has a molecular weight of between about 20,000 and 250,000.

14. The thermo-gelling solution of claim 12, wherein the compound is selected from the group consisting of cells, stem cells, peptides, growth factors nucleic acids, drugs, matrix components, and imaging agents.

15. The thermo-gelling system of claim 1 or 12, wherein osmolarity of said solution ranges from about 270 mOsmol/kg to about 340 mOsmol/kg.

16. A pharmaceutical composition comprising the thermo-gelling solution of claim 1 or 12 and a pharmaceutically-acceptable carrier.

17. The thermo-gelling solution of claim 1 or 12, wherein said solution is biocompatible.

18. A method of preparing a thermo-gelling solution, comprising the steps of:
    a) dissolving chitosan within an acidic aqueous solution to obtain an aqueous chitosan solution;
    b) maintaining said aqueous chitosan solution at a temperature below about 10° C.; and
    c) dissolving an inorganic salt in said aqueous chitosan solution to obtain said thermo-gelling solution, wherein said thermo-gelling solution is a solution at pH between about 6.0 and about 8.0 and forms a gel within a temperature range of about 20° C. to about 50° C.

19. The method of claim 18, wherein said inorganic salt is ammonium hydrogen phosphate.

20. The method of claim 19, wherein said thermo-gelling solution is a solution at pH between about 6.5 and about 7.5.

21. The method of claim 20, wherein said thermo-gelling solution is a solution at pH between about 7.0 and about 7.2.

22. The method of claim 20, wherein said thermo-gelling solution forms a gel within a temperature range from about 35° C. to about 45° C.

23. The method of claim 22, wherein said thermo-gelling solution forms a gel at a temperature of about 37° C.

24. A method for administering the pharmaceutical composition of claim 16 to a subject in need thereof, said method comprising applying said pharmaceutical composition to said subject.

* * * * *